(12) United States Patent
Mercenier et al.

(10) Patent No.: US 8,383,587 B2
(45) Date of Patent: Feb. 26, 2013

(54) PREVENTION OF ALLERGY AT WEANING

(75) Inventors: Annick Mercenier, Bussigny (CH); Marie-Claire Fichot, Blonay (CH); Adrian Zuercher, Bern (CH)

(73) Assignee: Nectec S.A., Vevey (CH)

( * ) Notice: Subject to any disclaimer, the term of this patent is extended or adjusted under 35 U.S.C. 154(b) by 136 days.

(21) Appl. No.: 12/680,083

(22) PCT Filed: Sep. 19, 2008

(86) PCT No.: PCT/EP2008/062532
§ 371 (c)(1), (2), (4) Date: May 17, 2010

(87) PCT Pub. No.: WO2009/040310
PCT Pub. Date: Apr. 2, 2009

(65) Prior Publication Data
US 2011/0021428 A1    Jan. 27, 2011

(30) Foreign Application Priority Data
Sep. 26, 2007 (EP) ..................................... 07117286

(51) Int. Cl.
*A61K 38/18* (2006.01)
*A61P 17/00* (2006.01)
*A61P 37/08* (2006.01)
*C07K 14/495* (2006.01)

(52) U.S. Cl. ......... 514/8.9; 424/535; 426/583; 530/350; 530/833; 514/5.6

(58) Field of Classification Search ........................ None
See application file for complete search history.

(56) References Cited

U.S. PATENT DOCUMENTS

| | | | |
|---|---|---|---|
| 6,403,142 | B1 | 6/2002 | McDaniel, III et al. |
| 6,733,770 | B1 | 5/2004 | Garcia-Rodenas et al. |
| 2004/0102377 | A1 | 5/2004 | Perrin et al. |
| 2010/0272708 | A1 * | 10/2010 | Juneau et al. ............... 424/130.1 |

FOREIGN PATENT DOCUMENTS

| | | |
|---|---|---|
| EP | 0313515 | 5/1989 |
| EP | 0322589 | 7/1989 |
| EP | 0827697 | 3/1998 |
| EP | 0880902 | 12/1998 |
| EP | 1803358 | 7/2007 |
| WO | WO9200994 | 1/1992 |
| WO | WO2005067962 | 7/2005 |

OTHER PUBLICATIONS

Hawkes et al. Variations in transforming growth factor beta in human milk are not related to levels in plasma. Cytokine. Feb. 21, 2002;17(4):182-6.*
Infant Formulas [online], Mar. 16, 2007 [retrieved on Feb. 7, 2012]. Retrieved from the Internet<URL: http://depts.washington.edu/growing/Nourish/Ftable.htm>.*
M. Li et al., "Transforming Growth Factor-β Regulation of Immune Responses," Annu. Rev. Immunol., 2006, vol. 24, pp. 99-146.
W. Oddy et al., "TGF-β in human milk is associated with wheeze in infancy," J Allergy Clin Immunol., Oct. 2003, pp. 723-728.
Penttila, I., "Effect of Transforming Growth Factor-Beta and Formula Feeding on Systemic Immune Responses to Dietary β-Lactoglobulin in Allergy-Prone Rats," Pediatric Research, vol. 59, No. 5, 2006, pp. 650-655.
Okamoto, A.,et al., "Suppression of serum IgE response and systemic anaphylaxis in a food allergy model by orally administered high-dose TGF-β," International Immunology, vol. 17, No. 6, 2005, pp. 705-712.
Fritsché, R., et al., "Induction of systemic immunologic tolerance to β-lactoglobulin by oral administration of a whey protein hydrolysate," J. Allergy Clin. Immunol., vol. 100, No. 2, 1997, pp. 266-273.
Kalliomäki, M., et al., "Transforming growth factor-β in breast milk: A potential regulator of atopic disease at an early age," J. Allergy Clin. Immunol., vol. 104, No. 6, 1999, pp. 1257-1257.
Fritsché, R., et al., "Determination of Cow Milk Formula Allergenicity in the Rat Model by in vitro Mast Cell Triggering and in vivo IgE Induction," Int. Arch. Aller and Appl Imm., vol. 93, 1990, pp. 289-293.
Fritsché, R., "Induction of Oral Tolerance to Cow's Milk Proteins in Rats Fed with a Whey Protein Hydrolysate," Nutrition Research, vol. 18, No. 8, 1998, pp. 1335-1341.
International Search Report for International Application No. PCT/EP2008/062532 mailed Jul. 11, 2008.
Written Opinion for International Application No. PCT/EP2008/062532 mailed Jul. 11, 2008.

* cited by examiner

*Primary Examiner* — David Romeo
(74) *Attorney, Agent, or Firm* — K&L Gates LLP

(57) ABSTRACT

A nutritional composition comprising a partially hydrolysed milk protein having a degree of hydrolysis between 15 and 25% and 50 to 1000 nanograms of TGF-β per 100 ml of ready to consume composition and methods for the primary prevention of allergic reactions to newly introduced dietary protein at weaning and the prevention of development of atopic diseases in a young mammal at weaning comprising feeding to the young mammal a therapeutic amount of the composition are disclosed.

6 Claims, No Drawings

PREVENTION OF ALLERGY AT WEANING

FIELD OF THE INVENTION

This invention relates to a nutritional composition and to the use of this composition for reducing the risk of development of allergy and atopic diseases during the weaning process.

BACKGROUND TO THE INVENTION

Food allergies, of which the first to occur in life is cows' milk allergy, are caused, in most cases, by a reaction to proteins in the food. In the early years of life the immune system is still developing and may fail to develop tolerance to dietary antigens (this may also be described as insufficient induction of oral tolerance). The result is that the baby or child or young animal mounts an exaggerated immune response to the dietary protein and develops an allergic response to it. Food allergies may affect not only humans but also other mammals such as dogs and cats.

Usually, food hypersensitivity develops just after a susceptible baby, child or young animal first encounters a new food containing potential allergens. Apart from its mother's milk, the first dietary proteins generally encountered by human babies at least are cows' milk proteins and, as noted above, cows' milk allergy is the most common food allergy in human babies. It is generally accepted that babies with established cows' milk allergy have an increased risk of developing allergies to other dietary proteins such as egg and cereal proteins. These allergies may manifest themselves clinically as atopic diseases such as atopic dermatitis, eczema and asthma. Even those babies who have successfully developed oral tolerance to cows' milk proteins may subsequently develop allergies to other dietary proteins such as egg and cereal proteins when these are introduced into the diet at weaning.

From a dietary point of view there are only two ways to treat an established allergy—either foods containing the allergen must be avoided altogether, or the foods must be treated to decrease their allergenic potential, for example by extensive hydrolysis. Infant formulas containing extensively hydrolysed cows' milk proteins (peptides consisting of not more than five amino acids) are manufactured for this latter purpose. Similarly it has already been proposed, in U.S. Pat. No. 6,403,142 for example, to prepare petfoods with reduced allergenicity for companion animals where it is suspected that the animal has developed a food allergy. However, exclusion diets have the disadvantages that compliance is low because available foodstuffs are very restricted in the case of avoidance diets and because of poor taste in the case of use of extensively hydrolysed products. Further, there is always a danger that intact allergens will nevertheless be encountered.

Therefore, products have been devised which help to reduce the risk of developing the allergy in the first place, particularly for children thought to be at risk of the same (that is, children having at least one close family member who suffers from an allergy). One example of such products is the infant formulas based on partially hydrolysed whey proteins sold under the trade marks NAN HA1 and NAN HA2. These products have been demonstrated to actively induce oral tolerance to cows' milk proteins. Fritsché et al. (J. Allergy Clin. Immunol, Vol 100, No. 2, pages 266-273, 1997) have shown using animal models that enzymatic hydrolysates of cow's milk proteins with a degree of hydrolysis of 18% were able to induce oral tolerance to intact cow's milk proteins whereas hydrolysates with a degree of hydrolysis of 28% were not. Results of these experiments showed that preventive feeding of rats with such a moderately hydrolysed cow's milk formula, whose allergenicity had been reduced over 100 times as compared to a standard formula, suppressed specific IgE and mediator release from intestinal mast cells, both parameters of an immediate type allergic reaction. This work demonstrated that for cows' milk proteins it is possible to define a degree of enzymatic hydrolysis whereby the capacity of the peptides to induce oral tolerance is maintained whilst their allergenicity is substantially reduced.

Transforming growth factor $\beta$, a bioactive peptide found in human milk has been identified as a potential regulator of atopic disease. A meta-analysis has provided evidence for an overall allergy preventing effect of TGF-$\beta$ in human milk (Gdalevich, 2001). According to Kalliomaki et al (J Allergy Clin. Immunol. 1999 December; 104(6):1251-7), the TGF-beta in colostrum may prevent the development of atopic disease during exclusive breast-feeding and promote specific IgA production in human subjects. Similarly, Oddy et al reported a reduced incidence of wheezing (indicative of respiratory allergy development) in children that had been breast fed for a significant period and had therefore received a high total dose of TGF-$\beta$ compared to children who had been breast-fed for shorter periods (Oddy et al, J Allergy Clin Immunol). More recently, it has been shown in a rat model that the addition of TGF-$\beta$ to cows' milk formula reduced allergic sensitisation to cows' milk (Pentilla et al, Pediatr Research 2006).

The period during which young mammals are exclusively milk-fed is relatively short ranging from a few weeks for rats and mice to four to six months for human infants for example. After this period, other foodstuffs containing different dietary proteins are progressively introduced into the diet and the dependence on milk to provide all the nutrients necessary for growth and development is correspondingly reduced in a process commonly called weaning.

Generally, the next dietary protein encountered by young mammals is cereal protein which is introduced at the start of weaning, typically in the form of infant cereals for human infants. Cereal proteins may also provoke allergic reactions when first introduced into the diet of a young mammal even if milk proteins have already been successfully introduced. Thereafter, the young mammal may encounter in rapid succession other dietary proteins including egg, peanut, fish and meat with the risk in each case that an allergic response may result.

However, by comparison with milk proteins, relatively little attention has been paid to the primary prevention of allergic reactions to other dietary proteins such as cereal and egg proteins nor to the possibility of preventing the development of allergic reactions to other antigens such as pollen by means of a dietary intervention. Indeed, this may be an even greater concern given that allergy to cows' milk proteins usually disappears spontaneously between the age of two and five years whereas allergy to cereal and egg proteins for example is generally slower to disappear and may even persist throughout life.

There is, therefore, a need to facilitate the introduction of dietary proteins other than milk proteins into the diet of young mammals at weaning by reducing the risk of development of allergic responses to such proteins as well as a need to reduce the subsequent incidence of atopic diseases whether or not provoked by dietary antigens, particularly in infants at risk of development of allergic responses.

SUMMARY OF THE INVENTION

The present inventors have surprisingly discovered that the use of a combination of a partially hydrolysed milk protein and TGF-beta helps to induce tolerance to other dietary proteins such as cereal and egg proteins when these are introduced into the diet of young mammals at weaning whilst maintaining a previously established tolerance to cows' milk proteins.

Accordingly, in a first aspect, the present invention provides a nutritional composition comprising a partially hydrolysed milk protein having a degree of hydrolysis between 15 and 25% and 50 to 1000 nanograms of TGF-β per 100 ml of ready to consume composition.

The invention extends to a method for the primary prevention of allergic reactions to newly introduced dietary proteins in a young mammal at weaning comprising feeding to the young mammal during the weaning period a therapeutic amount of a composition comprising a partially hydrolysed milk protein having a degree of hydrolysis between 15 and 25% and TGF-β.

The invention further extends to a method for the primary prevention of atopic diseases in a young mammal at weaning comprising feeding to the young mammal during the weaning period a therapeutic amount of a composition comprising a partially hydrolysed milk protein having a degree of hydrolysis between 15 and 25% and TGF-β.

Atopic diseases such as atopic eczema, allergic rhinitis and asthma may be the clinical manifestations of an allergic response to a dietary protein or of an allergic response to another type of antigen such as an airborne antigen. The prevalence of asthma for example has dramatically increased in the recent decades most probably as a result from changes in environmental factors such as pathogens, allergens, air pollution and diet. It has been demonstrated that airborne antigens are efficiently transferred from the mother to infant through milk and that tolerance induction does not require the transfer of immunoglobulins. Breastfeeding-induced tolerance relies on the presence of TGF-β during lactation, is mediated by regulatory CD4+ T lymphocytes and is dependent on TGF-β signalling in T cells. In conclusion, breast milk-mediated transfer of an airborne antigen to the infant results in the induction of oral tolerance leading to antigen-specific protection from allergic airway disease. Without wishing to be bound by theory, the inventors believe that the surprising discovery that induction of tolerance to airborne antigens does not require the transfer of immunoglobulins but relies rather on the effects of TGF-β in breast milk leads to the realisation that it may be possible to reduce the risk of both allergic reactions to dietary proteins and development of atopic diseases by a nutritional intervention based on a partially hydrolysed milk protein in combination with TGF-β. In other words, the administration of a combination of partially hydrolysed milk protein with TGF-β during weaning when the infant is exposed for the first time to other dietary proteins such as egg proteins and cereal proteins helps to reduce the risk of sensitisation to the new proteins and subsequently the development of allergic reactions to such proteins as well as the risk of development of atopic diseases.

DETAILED DESCRIPTION OF THE INVENTION

In this specification, the following terms have the following meanings:—
"atopic disease" means the clinical manifestations of allergic sensitisation and includes atopic dermatitis, atopic eczema, allergic rhinitis and asthma;
"degree of hydrolysis" or "DH" of a protein means the number of peptide bonds in the intact protein which are cleaved during the hydrolysis divided by the number of peptide bonds in the intact protein expressed as a percentage; "infant" means a child under the age of 12 months;
"follow-on formula" means compositions intended for use by infants aged over four months and constituting the principal liquid element in the progressively diversified diet of such infants;
"oral tolerance" means an active state of immunological hyporesponsiveness to antigens delivered via the oral route;
"primary prevention of allergic reaction to a dietary protein" means prevention of establishment of such allergic reaction and includes reduction of risk of such an allergic reaction;
"TGF-β" or "transforming growth factor β designates a group of at least five distinct but closely related bioactive peptides designated TGF-β1, TGF-β2 etc and found inter alia in human milk (TGF-β1 and TGF-β2) (Li et al, Transforming Growth Factor-β Regulation of Immune Responses, Annu Rev. Immunol. 2006 24:99-146);
"weaning" means the introduction into the diet of a young mammal of foods other than its mother's milk or milk-based substitute such as infant formula;
"weaning period" means that period in the life of a young mammal starting with the introduction of foods other than its mothers milk or milk-based substitute therefore and ending with the cessation of breast feeding or administration of infant formula or follow-on formula.

All references to percentages are percentages by weight unless otherwise stated.

The invention provides a nutritional composition comprising a partially hydrolysed milk protein having a degree of hydrolysis between 15 and 25% and 50 to 1000 nanograms of TGF-β per 100 ml of ready to consume composition.

The milk protein may be whey protein, casein protein or a mixture thereof but preferably is whey protein. If whey protein is used, the degree of hydrolysis is preferably between 15 and 19%.

Preferably, the partially hydrolysed milk protein has a residual antigenicity at least 100 times less than that of intact whey protein. The residual allergenicity of the partially hydrolysed milk protein may be measured by the technique described by Fritsché et al (Int. Arch. Aller and Appl Imm., 93, 289-293, 1990). Such a partially hydrolysed milk protein and products containing it may be described as hypoallergenic in accordance with the provisions of EU Directive 96/4/EC.

Compositions according to the invention may be used in the weaning of young mammals including human infants and toddlers as well as the young of companion animals such as dogs and cats.

Preferably the nutritional composition of the invention is an infant formula, more preferably a follow-on formula for use by infants aged over four months.

The milk protein may be hydrolysed in any suitable manner known in the art. In the case of whey protein, a suitable process is described in European Patent No. 322,589, the contents of which are incorporated herein by reference. If the whey fraction used as the starting material is substantially lactose free, it is found that the protein suffers much less lysine blockage during the hydrolysis and subsequent thermal processing. This enables the extent of lysine blockage to be reduced from about 15% by weight of total lysine to less than about 10% by weight of lysine; for example about 7% by weight of lysine blockage which greatly improves the nutritional quality of the protein source.

The source of the whey protein may be acid whey, sweet whey, whey protein isolate or mixtures thereof. Preferably, however, the protein source is based on whey protein isolate or modified sweet whey. Sweet whey is a readily available by-product of cheese making and is frequently used in the manufacture of infant formulas based on cows' milk. However, sweet whey includes a component which is undesirably rich in threonine and poor in tryptophan called caseino-glyco-macropeptide (CGMP). Removal of the CGMP from sweet whey results in a protein fraction with a threonine content closer to that of human milk. A process for removing CGMP from sweet whey is described in EP 880902.

If modified sweet whey or whey protein isolate is used as the protein source, it is preferably supplemented by free histidine in an amount of from 0.1 to 3% by weight of the protein.

An infant formula of the present invention may comprise from 1.0 to 2.0 grams of partially hydrolysed whey protein per 100 ml of ready to consume formula, more preferably from 1.5 to 1.9 g/100 ml.

A follow-on formula of the present invention contains from 50 to 1000 nanograms of TGF-$\beta$ per 100 ml of ready to consume formula, more preferably from 50 to 500 nanograms per 100 ml and most preferably 200 to 300 nanograms per 100 ml. Preferably, a follow-on formula of the present invention contains both TGF-$\beta$1 and TGF-$\beta$2, more preferably in a ratio between 1:5 and 1:50.

TGF-$\beta$ may be added to the formula in the form of a whey protein fraction enriched in these bioactive peptides such as TM0301 or XP-828L from Armor Proteins, France or in the form of a polypeptide growth factor isolated from milk as described for example in EP 313515 or WO 92/00994. Alternatively, a recombinant TGF-$\beta$ may be used if preferred.

A follow-on formula according to the present invention may contain a carbohydrate source. Any carbohydrate source conventionally found in infant formulae such as lactose, saccharose, maltodextrin, starch and mixtures thereof may be used although the preferred source of carbohydrates is lactose. Preferably the carbohydrate source contributes between 35 and 65% of the total energy of the formula.

A follow-on formula according to the present invention may contain a source of lipids. The lipid source may be any lipid or fat which is suitable for use in infant formulas. Preferred fat sources include palm olein, high oleic sunflower oil and high oleic safflower oil. The essential fatty acids linoleic and $\alpha$-linolenic acid may also be added as may small amounts of oils containing high quantities of preformed arachidonic acid and docosahexaenoic acid such as fish oils or microbial oils. In total, the fat content is preferably such as to contribute between 30 to 55% of the total energy of the formula. The fat source preferably has a ratio of n-6 to n-3 fatty acids of about 5:1 to about 15:1; for example about 8:1 to about 10:1.

The follow-on formula may also contain all vitamins and minerals understood to be essential in the daily diet and in nutritionally significant amounts. Minimum requirements have been established for certain vitamins and minerals. Examples of minerals, vitamins and other nutrients optionally present in the infant formula include vitamin A, vitamin B1, vitamin B2, vitamin B6, vitamin B12, vitamin E, vitamin K, vitamin C, vitamin D, folic acid, inositol, niacin, biotin, pantothenic acid, choline, calcium, phosphorous, iodine, iron, magnesium, copper, zinc, manganese, chloride, potassium, sodium, selenium, chromium, molybdenum, taurine, and L-carnitine. Minerals are usually added in salt form. The presence and amounts of specific minerals and other vitamins will vary depending on the intended infant population.

If necessary, the formula may contain emulsifiers and stabilisers such as soy lecithin, citric acid esters of mono- and di-glycerides, and the like.

The formula may optionally contain other substances which may have a beneficial effect such as lactoferrin, nucleotides, nucleosides, and the like.

Finally, the formula may contain indigestible oligosaccharides such as galacto-oligosaccharides for example in an amount of from 0.3 to 7%.

The formula may be prepared in any suitable manner. For example, it may be prepared by blending together the partially hydrolysed milk protein, the carbohydrate source, and the fat source in appropriate proportions. If used, the emulsifiers may be included at this point. The TGF-$\beta$ may also be added at this point. The vitamins and minerals may be added at this point but are usually added later to avoid thermal degradation. Any lipophilic vitamins, emulsifiers and the like may be dissolved into the fat source prior to blending. Water, preferably water which has been subjected to reverse osmosis, may then be mixed in to form a liquid mixture. The temperature of the water is conveniently about 50° C. to about 80° C. to aid dispersal of the ingredients. Commercially available liquefiers may be used to form the liquid mixture. The liquid mixture is then homogenised; for example in two stages.

The liquid mixture may then be thermally treated to reduce bacterial loads, by rapidly heating the liquid mixture to a temperature in the range of about 80° C. to about 150° C. for about 5 seconds to about 5 minutes, for example. This may be carried out by steam injection, autoclave or by heat exchanger; for example a plate heat exchanger.

Then, the liquid mixture may be cooled to about 60° C. to about 85° C.; for example by flash cooling. The liquid mixture may then be again homogenised; for example in two stages at about 10 MPa to about 30 MPa in the first stage and about 2 MPa to about 10 MPa in the second stage. The homogenised mixture may then be further cooled to add any heat sensitive components; such as vitamins and minerals. The pH and solids content of the homogenised mixture are conveniently adjusted at this point.

The homogenised mixture is transferred to a suitable drying apparatus such as a spray drier or freeze drier and converted to powder. The powder should have a moisture content of less than about 5% by weight. The TGF-$\beta$ may be added at this point by dry mixing if not added previously.

If a liquid product is preferred, the homogenised mixture may be sterilised then aseptically filled into suitable containers.

EXAMPLE 1

An example of the composition of a follow-on formula according to the present invention is given below. This composition is given by way of illustration only.

| Nutrient | per 100 kcal | per litre |
|---|---|---|
| Energy (kcal) | 100 | 670 |
| Partially hydrolysed whey protein (g) | 1.83 | 12.3 |
| Fat (g) | 5.3 | 35.7 |
| Linoleic acid (g) | 0.79 | 5.3 |
| $\alpha$-Linolenic acid (mg) | 101 | 675 |
| Lactose (g) | 11.2 | 74.7 |
| Prebiotic (90% GOS, 10% inulin) (g) | 1.2 | 8.0 |
| Minerals (g) | 0.37 | 2.5 |
| Na (mg) | 23 | 150 |
| K (mg) | 89 | 590 |
| Cl (mg) | 64 | 430 |
| Ca (mg) | 62 | 410 |
| P (mg) | 31 | 210 |
| Mg (mg) | 7 | 50 |
| Mn (µg) | 8 | 50 |

-continued

| Nutrient | per 100 kcal | per litre |
|---|---|---|
| Se (μg) | 2 | 13 |
| Vitamin A (μg RE) | 105 | 700 |
| Vitamin D (μg) | 1.5 | 10 |
| Vitamin E (mg TE) | 0.8 | 5.4 |
| Vitamin K1 (μg) | 8 | 54 |
| Vitamin C (mg) | 10 | 67 |
| Vitamin B1 (mg) | 0.07 | 0.47 |
| Vitamin B2 (mg) | 0.15 | 1.0 |
| Niacin (mg) | 1 | 6.7 |
| Vitamin B6 (mg) | 0.075 | 0.50 |
| Folic acid (μg) | 9 | 60 |
| Pantothenic acid (mg) | 0.45 | 3 |
| Vitamin B12 (μg) | 0.3 | 2 |
| Biotin (μg) | 2.2 | 15 |
| Choline (mg) | 10 | 67 |
| Fe (mg) | 1.2 | 8 |
| I (μg) | 15 | 100 |
| Cu (mg) | 0.06 | 0.4 |
| Zn (mg) | 0.75 | 5 |
| TGF-β (ng) | 448 | 3000 |
| of which:  TGF-β1 | 45 | 300 |
| TGF-β2 | 403 | 2700 |

The invention claimed is:

1. A nutritional composition comprising:
   from 1.0 to 2.0 grams of partially hydrolysed whey protein per 100 ml of ready to consume composition, wherein the partially hydrolysed whey protein has a degree of hydrolysis ranging between 15 and 25%, and
   50 to 1000 nanograms of TGF-β per 100 ml of ready to consume composition, the TGF-β being a mixture of TGF-β1 and TGF-β2 at a ratio of TGF-β1 to TGF-β2 from 1:5 to 1:50.

2. A composition according to claim 1, wherein the composition is a follow-on formula.

3. A composition according to claim 1, wherein the partially hydrolysed milk protein has a residual antigenicity that is at least 100 times less than that of the intact protein.

4. A composition according to claim 1, wherein the degree of hydrolysis of the partially hydrolysed whey protein is between 15 and 19%.

5. A composition according to claim 1 comprising from 1.2 to 1.9 grams of partially hydrolysed whey protein per 100 ml of ready to consume composition.

6. A composition according to claim 1 comprising 200 to 300 nanograms of TGF-β per 100 ml of ready to consume composition.

* * * * *